US005719097A

United States Patent [19]
Chang et al.

[11] Patent Number: 5,719,097
[45] Date of Patent: Feb. 17, 1998

[54] CATALYST COMPRISING A MODIFIED SOLID OXIDE

[76] Inventors: Clarence D. Chang, 11 Murray Pl., Princeton, N.J. 08540; Jose G. Santiesteban, 7 Richie La.; David L. Stern, 1712 Polo Run Dr., both of Yardley, Pa. 19067

[21] Appl. No.: 679,238

[22] Filed: Jul. 22, 1996

Related U.S. Application Data

[63] Continuation of Ser. No. 95,884, Jul. 22, 1993, abandoned.

[51] Int. Cl.[6] ............ B01J 23/00; B01J 23/42; B01J 23/40
[52] U.S. Cl. ............ 502/325; 502/326; 502/333; 502/334; 502/335; 502/336; 502/349; 502/350; 502/352
[58] Field of Search ............ 502/325, 326, 502/333, 334, 335, 336, 349, 350, 352

[56] References Cited

U.S. PATENT DOCUMENTS

| | | | |
|---|---|---|---|
| 4,783,575 | 11/1988 | Schmidt et al. | 585/748 |
| 4,918,041 | 4/1990 | Hollstein et al. | 502/217 |
| 4,956,519 | 9/1990 | Hollstein et al. | 585/751 |
| 5,113,034 | 5/1992 | Soled et al. | 585/510 |
| 5,176,897 | 1/1993 | Lester | 502/309 |
| 5,236,692 | 8/1993 | Nagashima | 423/584 |
| 5,422,327 | 6/1995 | Soled et al. | 502/242 |

FOREIGN PATENT DOCUMENTS

| | | |
|---|---|---|
| 504741 | 9/1992 | European Pat. Off. . |
| 0 585 065 | 3/1994 | European Pat. Off. . |
| 1288339 | 4/1989 | Japan . |
| WO 94/14732 | 7/1994 | WIPO . |

OTHER PUBLICATIONS

Iglesia, E. Soled, S.L., and Kramer, G.M., Isomerization of Alkanes on Sulfated Zirconia: Promotion by Pt and by Adamantyl Hydride Transfer Species, Journal of Catalysis 144, 238–253 (1993) No Month Available.

Hsu C.Y., Heimbuch, C.R., Armes, C.T., and Gates, B.C., A Highly Active Solid Superacid Catalyst for n–Butane Isomerization: a Sulfated Oxide Containing Iron, Manganese and Zirconium, J. Chem. Soc., Chem. Commun., 1645 (1992) No Month Available.

Hino, M. et al., "Synthesis of Solid Superacid of Tungsten Oxide Supported On Zirconia and its Catalytic Action for Reactions of Butane and Pentane," J.Chem.Soc., Chem. Commun., 1259–1260 (1988) No Month Available.

Proceedings 9th Intern. Congress on Catalysis, vol. 4, Oxide Catalysts and Catalyst Development, Arata et al., 1727–1734 (1988) No Month Available.

*Primary Examiner*—Glenn A. Caldarola
*Assistant Examiner*—Elizabeth D. Wood

[57] ABSTRACT

There is provided a catalyst comprising a hydrogenation/dehydrogenation component, such as a noble metal, and an acidic solid component comprising a Group IVB metal oxide modified with an oxyanion of a Group VIB metal. An example of this catalyst is zirconia, modified with tungstate and platinum. There is also provided a method for preparing this catalyst. This catalyst may be used, for example, to isomerize $C_4$ to $C_8$ paraffins. The feed to this paraffin isomerization reaction may, optionally, include cyclic hydrocarbons, such as benzene or cyclohexane, which may undergo ring opening reactions during the course of the isomerization reaction.

17 Claims, No Drawings

CATALYST COMPRISING A MODIFIED SOLID OXIDE

This application is a continuation of U.S. Ser. No. 08/095,884 filed Jul. 22, 1993 and now abandoned.

There is provided a catalyst comprising a hydrogenation/dehydrogenation component, such as a noble metal, and an acidic solid component comprising a Group IVB metal oxide modified with an oxyanion of a Group VIB metal. This catalyst may be used, for example, to isomerize $C_4$ to $C_8$ paraffins. The feed to this paraffin isomerization reaction may, optionally, include cyclic hydrocarbons, such as benzene or cyclohexane, which may undergo ring opening reactions during the course of the isomerization reaction.

The isomerization of paraffins, especially light paraffins, is an established refining process which is traditionally used to provide additional feedstock for alkylation units or to convert relatively low octane linear paraffins to higher octane, branched chain isomers which can be blended into the gasoline pool. Straight chain paraffins such as n-butane, n-pentane and n-hexane are converted to the corresponding isoparaffins by various isomerization processes which may use various types of catalysts.

Non-regenerable Lewis and Bronsted acid catalysts may be used, for example, as disclosed in U.S. Pat. Nos. 3,766,286; 3,852,184; 3,855,346; 3,839,489; 4,144,282; and 4,814,544. Commerical processes of this type have been developed by various companies including Phillips Petroleum Company (Catalytic Isomerization) and Shell Development Company (Liquid Phase Isomerization).

An alternative type of catalyst used in a number of commercial isomerization processes comprises a metal hydrogenation/dehydrogenation component, usually platinum, on a porous support. An example of this process is the Penex process (UOP) in which the isomerization is carried out in the presence of hydrogen and a platinum catalyst. The Iso-Kel process (M. W. Kellogg) also employs a precious metal catalyst with hydrogen circulation and the Pentafining (Arco/Englehardt) and Butamer (UOP) processes also employ platinum on supports with external hydrogen circulation. Processes of this kind are disclosed, for example, in U.S. Pat. Nos. 4,834,866 (Schmidt) and U.S. Pat. No. 4,783,575 (Schmidt).

Isomerization processes utilizing metal components on supports comprising a molecular sieve are disclosed in U.S. Pat. Nos. 3,842,114 (Sie); U.S. Pat. No. 3,836,597 (Sie); U.S. Pat. No. 4,778,944 (Zarchy) and U.S. Pat. No. 4,374,296 (Haag).

Paraffin isomerization catalysts may also be employed as ring opening catalysts for the removal of cyclic aromatic precursors from reformer feedstocks as disclosed in U.S. Pat. No. 4,783,575 (Schmidt) and U.S. Pat. No. 4,834,866 (Schmidt). For example, cyclohexane, a precursor of benzene, may be isomerized to a mixture of branched paraffins which are only partly aromatized in the reformer so as to minimize the production of benzene. U.S. Pat. No. 3,631,117 describes a process for the hydroisomerization of cyclic hydrocarbons that uses a zeolite supported Group VIII metal as a catalyst for ring opening and paraffin isomerization. The utilization of paraffin isomerization for ring opening aromatic precursors, especially cyclohexane, is likely to become more important in the future as environmental regulations limit the aromatic content, particularly the benzene content, of motor gasoline.

SUMMARY

There is provided a catalyst comprising (i) a hydrogenation/dehydrogenation component comprising a noble metal and (ii) an acidic solid component comprising a Group IVB metal oxide modified with an oxyanion of a Group VIB metal.

There is also provided a method for preparing this catalyst comprising comprising (i) a hydrogenation/dehydrogenation component comprising a noble metal and (ii) an acidic solid component comprising a Group IVB metal oxide modified with an oxyanion of a Group VIB metal, said method comprising the steps of:

(a) contacting the hydroxide or hydrated oxide of a Group IVB metal with an aqueous solution comprising a source of an oxyanion of a Group VIB metal under conditions sufficient to form a solid material comprising oxygen, Group IVB metal and Group VI metal; and (b) combining said solid material of step (a) with a source of a noble metal.

There is also provided a process for converting an organic compound, e.g., a hydrocarbon, over a catalyst comprising (i) a hydrogenation/dehydrogenation component comprising a noble metal and (ii) an acidic solid component comprising a Group IVB metal oxide modified with an oxyanion of a Group VIB metal.

EMBODIMENTS

The catalyst described herein comprises an oxide of a Group IVB metal, preferably zirconia or titania. This Group IVB metal oxide is modified in two ways. According to one modification, the Group IVB metal oxide is modified with an oxyanion of a Group VIB metal, such as an oxyanion of tungsten, such as tungstate. The modification of the Group IVB metal oxide with the oxyanion of the Group VIB metal imparts acid functionality to the material. The modification of a Group IVB metal oxide, particularly, zirconia, with a Group VIB metal oxyanion, particularly tungstate, is described in U.S. Pat. No. 5,113,034; in Japanese Kokai Patent Application No. Hei 1 [1989]-288339; and in an article by K. Arata and M. Hino in *Proceedings 9th International Congress on Catalysis*, Volume 4, pages 1727–1735 (1988), the entire disclosures of these publications are expressly incorporated herein by reference.

According to another modification of the Group IVB metal oxide described herein, a hydrogenation/dehydrogenation component is combined with the Group IV metal oxide. This hydrogenation/dehydrogenation component imparts the ability of the material to catalyze the addition of hydrogen to or the removal of hydrogen from organic compounds, such as hydrocarbons, optionally substituted with one or more heteroatoms, such as oxygen, nitrogen, metals or sulfur, when the organic compounds are contacted with the modified material under sufficient hydrogenation or dehydrogenation conditions.

Examples of hydrogenation/dehydrogenation components include the oxide, hydroxide or free metal (i.e., zero valent) forms of Group VIII metals (i.e., Pt, Pd, Ir, Rh, Os, Ru, Ni, Co and Fe), Group IVA metals (i.e., Sn and Pb), Group VB metals (i.e., Sb and Bi) and Group VIIB metals (i.e., Mn, Tc and Re). The present catalyst comprises one or more catalytic forms of one or more noble metals (i.e., Pt, Pd, Ir, Rh, Os or Ru). Combinations of catalytic forms of such noble or non-noble metals, such as combinations of Pt with Sn, may be used. The valence state of the metal of the hydrogenation/dehydrogenation component is preferably in a reduced valance state, e.g., when this component is in the form of an oxide or hydroxide. The reduced valence state of this metal may be attained, in situ, during the course of a reaction, when a reducing agent, such as hydrogen, is included in the feed to the reaction.

For the purposes of the present disclosure, the expression, Group IVB metal oxide modified with an oxyanion of a Group VIB metal, is intended to connote a material comprising, by elemental analysis, a Group IVB metal, a Group VIB metal and oxygen, with 30 more acidity than a simple mixture of separately formed Group IVB metal oxide mixed with a separately formed Group VIB metal oxide or oxyanion. The present Group IVB metal, e.g., zirconium, oxide modified with an oxyanion of a Group VIB metal, e.g., tungsten, is believed to result from an actual chemical interaction between a source of a Group IVB metal oxide and a source of a Group VIB metal oxide or oxyanion.

This chemical interaction is discussed in the aforementioned article by K. Arata and M. Hino in *Proceedings 9th International Congress on Catalysis*, Volume 4, pages 1727–1735 (1988). In this article, it is suggested that solid superacids are formed when sulfates are reacted with hydroxides or oxides of certain metals, e.g., Zr. These superacids are said to have the structure of a bidentate sulfate ion coordinated to the metal, e.g., Zr. In this article, it is further suggested that a superacid can also be formed when tungstates are reacted with hydroxides or oxides of Zr. The resulting tungstate modified zirconia materials are theorized to have an analogous structure to the aforementioned superacids comprising sulfate and zirconium, wherein tungsten atoms replace sulfur atoms in the bidentate structure.

Although it is believed that the present catalysts may comprise the bidentate structure suggested in the aforementioned article by Arata and Hino, the particular structure of the catalytically active site in the present Group IVB metal oxide modified with an oxyanion of a Group VIB metal has not yet been confirmed, and it is not intended that this catalyst component should be limited to any particular structure.

Other elements, such as alkali (Group IA) or alkaline earth (Group IIA) compounds may optionally be added to the present catalyst to alter catalytic properties. The addition of such alkali or alkaline earth compounds to the present catalyst may enhance the catalytic properties of components thereof, e.g., Pt or W, in terms of their ability to function as a hydrogenation/dehydrogenation component or an acid component.

The Group IVB metal (i.e., Ti, Zr or Hf) and the Group VIB metal (i.e., Cr, Mo or W) species of the present catalyst are not limited to any particular valence state for these species. These species may be present in this catalyst in any possible positive oxidation value for these species. Subjecting the catalyst, e.g., when the catalyst comprises tungsten, to reducing conditions, e.g., believed to be sufficient to reduce the valence state of the tungsten, may enhance the overall catalytic ability of the catalyst to catalyze certain reactions, e.g., the isomerization of n-hexane.

Suitable sources of the Group IVB metal oxide, used for preparing the present catalyst, include compounds capable of generating such oxides, such as oxychlorides, chlorides, nitrates, etc., particularly of zirconium or titanium. Alkoxides of such metals may also be used as precursors or sources of the Group IVB metal oxide. Examples of such alkoxides include zirconium n-propoxide and titanium i-propoxide. Preferred sources of a Group IVB metal oxide are zirconium hydroxide, i.e., $Zr(OH)_4$, and hydrated zirconia. The expression, hydrated zirconia, is intended to connote materials comprising zirconium atoms covalently linked to other zirconium atoms via bridging oxygen atoms, i.e., Zr-O-Zr, further comprising available surface hydroxy groups. These available surface hydroxyl groups are believed to react with the source of an anion of a Group IVB metal, such as tungsten, to form the present acidic catalyst component. As suggested in the aforementioned article by K. Arata and M. Hino in *Proceedings 9th International Congress on Catalysis*, Volume 4, pages 1727–1735 (1988), precalcination of $Zr(OH)_4$ at a temperature of from about 100° C. to about 400° C. results in a species which interacts more favorably with tungstate. This precalcination is believed to result in the condensation of ZrOH groups to form a polymeric zirconia species with surface hydroxyl groups. This polymeric species is referred to herein as a form of a hydrated zirconia.

Treatment of hydrated zirconia with a base solution prior to contact with a source of tungstate may be preferable. More particularly, as demonstrated in Examples recited hereinafter, especially in Examples 16–25, refluxing hydrated zirconia in an $NH_4OH$ solution having a pH of greater than 7 was beneficial. Without wishing to be bound by any theory, it is theorized that the base-treated, hydrated zirconia is better because it has higher surface area. It is also theoretically possible that the base treatment alters surface hydroxyl groups on the hydrated zirconia, possibly in a manner which promotes a more desirable interaction with the source of tungstate later used.

Suitable sources for the oxyanion of the Group VIB metal, preferably molybdenum or tungsten, include, but are not limited to, ammonium metatungstate or metamolybdate, tungsten or molybdenum chloride, tungsten or molybdenum carbonyl, tungstic or molybdic acid and sodium tungstate or molybdate.

The hydrogenation/dehydrogenation component of the present catalyst may be derived from Group VIII metals, such as platinum, iridium, osmium, palladium, rhodium, ruthenium, nickel, cobalt, iron and mixtures of two or more thereof. These components may optionally be mixed with components derived from Group IVA metals, preferably Sn, and/or components derived from Group VIIB metals, preferably rhenium and manganese. These components may be added to the catalyst by methods known in the art, such as ion exchange, impregnation or physical admixture. For example, salt solutions of these metals may be contacted with the remaining catalyst components under conditions sufficient to combine the respective components. The metal containing salt is preferably water soluble. Examples of such salts include chloroplatinic acid, tetraammineplatinum complexes, platinum chloride, tin sulfate and tin chloride.

The present catalyst may be prepared, for example, by impregnating the hydroxide or oxide, particularly the hydrated oxide, of the Group IVB metal with an aqueous solution containing an anion of the Group VIB metal, preferably tungstate or molybdate, followed by drying. Calcination of the resulting material may be carried out, preferably in an oxidizing atmosphere, at temperatures from about 500° C. to about 900° C., preferably from about 700° C. to about 850° C., and more preferably from about 750° C. to about 825° C. The calcination time may be up to 48 hours, preferably for about 0.5–24 hours, and more preferably for about 1.0–10 hours. In a most preferred embodiment, calcination is carried out at about 800° C. for about 1 to about 3 hours. The hydrogenation/dehydrogenation component of the catalyst (e.g., Group VIII metal, Group VIIB metal, etc.) may be added after or before the calcination step by techniques known in the art, such as impregnation, coimpregnation, coprecipitation, physical admixture, etc. The hydrogenation/dehydrogenation component may also be combined with the remaining catalyst components before or after these remaining components are combined with a binder or matrix material as described hereinafter.

When a source of the hydroxide or hydrated oxide of zirconium is used, calcination, e.g., at temperatures greater than 500° C., of the combination of this material with a source of an oxyanion of tungsten may be needed to induce the theorized chemical reaction which imparts the desired degree of acidity to the overall material. However, when more reactive sources of zirconia are used, it is possible that such high calcination temperatures may not be needed.

In the present catalyst, of the Group IVB oxides, zirconium oxide is preferred; of the Group VIB anions, tungstate is preferred; and of the hydrogenation/dehydrogenation components, platinum and/or platinum-tin are preferred.

Qualitatively speaking, elemental analysis of the present catalyst will reveal the presence of Group IVB metal, Group VIB metal and oxygen. The amount of oxygen measured in such an analysis will depend on a number of factors, such as the valence state of the Group IVB and Group VIB metals, the form of the hydrogenation/dehydrogenation component, moisture content, etc. Accordingly, in characterizing the composition of the present catalyst, it is best not to be restricted by any particular quantities of oxygen. In functional terms, the amount of Group VIB oxyanion in the present catalyst may be expressed as that amount which increases the acidity of the Group IVB oxide. This amount is referred to herein as an acidity increasing amount. Elemental analysis of the present catalyst may be used to determine the relative amounts of Group IVB metal and Group VIB metal in the catalyst. From these amounts, mole ratios in the form of $XO_2/YO_3$ may be calculated, where X is said Group IVB metal, assumed to be in the form $XO_2$, and Y is said Group VIB metal, assumed to be in the form of $YO_3$. It will be appreciated, however, that these forms of oxides, i.e., $XO_2$ and $YO_3$, may not actually exist, and are referred to herein simply for the purposes of calculating relative quantities of X and Y in the present catalyst. The present catalysts may have calculated mole ratios, expressed in the form of $XO_2/YO_3$, where X is at least one Group IVB metal (i.e., Ti, Zr, and Hf) and Y is at least one Group VIB metal (i.e., Cr, Mo, or W), of up to 1000, e.g., up to 300, e.g., from 2 to 100, e.g., from 4 to 30.

The amount of hydrogenation/dehydrogenation component may be that amount which imparts or increases the catalytic ability of the overall material to catalytically hydrogenate or dehydrogenate a hydrogenatable or dehydrogenatable organic compound under sufficient hydrogenation or dehydrogenation conditions. This amount is referred to herein as a catalytic amount. Quantitatively speaking, the present catalyst may comprise, for example, from about 0.001 to about 5 wt %, e.g., from about 0.1 to about 2 wt %, of the hydrogenation/dehydrogenation component, especially when this component is a noble metal.

The catalyst described herein may be used as a catalyst for isomerizing $C_4$ to $C_8$ paraffins. Suitable feeds contain substantial amounts of normal and/or singly branched low octane $C_4$ to $C_8$ hydrocarbons. The feed may also contain appreciable amounts of $C_6$ and $C_7$ cyclic paraffins which may undergo ring-opening reactions.

The present isomerization process may be carried out by contacting the hydrocarbon feed in either liquid or gas phase with the solid catalyst at temperatures less than 500° C., preferably less than 350° C., preferably less than 300° C., and at pressure in the range from 1 to 200 atmospheres, preferably from 1 to 100 atmospheres, more preferably 5 to 50 atmospheres. The isomerization process may be carried out either in the presence or absence of hydrogen, more preferably in the presence of hydrogen. The mole ratio of hydrogen to hydrocarbon is preferably in the range of 0.01:1 to 10:1.

It may be desirable to incorporate the present catalyst with another material to improve its properties. Such materials include active and inactive materials and synthetic or naturally occurring zeolites as well as inorganic materials such as clays, silica, and/or metal oxides. The latter may be either naturally occurring or in the form of gelatinous precipitates, sols, or gels including mixtures of silica and metal oxides.

It is noted that the present catalyst need not contain any sulfate ion (U.S. Pat. No. 4,918,041), and is believed to be more stable and also to be much easier to regenerate than sulfated catalysts, such as the superacid sulfated catalysts referred to in the aforementioned article by K. Arata and M. Hino in *Proceedings 9th International Congress on Catalysis,* Volume 4, pages 1727–1735 (1988).

In the present isomerization process, n-paraffinic and mono-methyl branched paraffinic components are isomerized to higher branched paraffins which are generally better octane boosters. By way of illustration, the significance of these reactions can be gleaned from a review of the following table of Octane Numbers of Pure Hydrocarbons from P. H. Emmett, ed., *Catalysis,* Vol. VI (1958).

| Octane Numbers of Pure Hydrocarbons | |
| --- | --- |
| Hydrocarbon | Blending Research Octane Number (clear) |
| Paraffins: | |
| n-heptane | 0 |
| 2-methylhexane | 41 |
| 3-methylhexane | 56 |
| 2,2-dimethylpentane | 89 |
| 2,3-dimethylpentane | 87 |
| 2,2,3-trimethylbutane | 113 |

The feedstock for the present process may be one which contains significant amounts of $C_5+$ normal and/or slightly branched paraffins. In addition, the feedstock may contain monocyclic aromatic compounds and/or cyclic paraffins, such as cyclohexane. Among the hydrocarbons having 6 or less carbon atoms in the feedstock, at least 1 wt. %, e.g., at least 5 wt. %, e.g., at least 10 wt. %, e.g., at least 20 wt. %, e.g., at least 30 wt. %, of these hydrocarbons may be cyclic hydrocarbons, e.g., aromatics or cyclic paraffins.

The present catalyst may be used to isomerize $C_4$–$C_8$ paraffin hydrocarbons, either as pure compounds or mixtures. In refinery operations, the paraffins will normally be present in mixtures and, in addition to the $C_4$–$C_8$ materials, may contain hydrocarbons boiling outside this range; cyclo-paraffins and aromatics may also be present. Thus, the feed will comprise $C_4$–$C_8$ paraffins such as butane, pentane, hexane and these may be present in refinery streams such as raffinate cuts from solvent extraction units, reformer feedstock or pyrolysis gasoline from ethylene crackers. The feeds may also contain cyclic hydrocarbons, e.g., in the form of $C_6+$ naphthas; the cyclic materials in such feeds may undergo ring opening reactions in the presence of the catalyst with its associated metal component, to form paraffins which then undergo isomerization to iso-paraffins which can be separated from the cyclics by fractionation with the cyclics being recycled to extinction. In addition to pure paraffin feeds ($C_4$–$C_8$), mixed paraffin-olefin feeds containing significant levels of olefin may be utilized. The isomerization is carried out in the presence of the catalyst, preferably in the presence of hydrogen. Reaction temperatures are suitably in the range of about 200° to 800° F. (about 93° to 425° C.); temperatures outside this range may be utilized although they are normally less preferred; temperatures from about 300° to 700° F. (about 149° to 370° C.) are typical. Pressures will normally be up to about 1000 psig (about 7,000 kPa abs.) although there is no reason why higher pressures should not be utilized. Lower pressures, in the range of about 50 to 100 psig (about 445 to 790 kPa abs.) may readily be employed and the use of relatively low pressures within this range will generally be preferred in order to permit the use of low pressure equipment. The isomerization is usually carried out in the presence of hydrogen, typically at a molar ratio relative to the feed from 0.01 to 10:1 and usually from 0.5:1 to 2:1. Space velocities are typically from 0.1 to 10 LHSV and usually from 0.5 to 5 LHSV. When an additional acidic material (Lewis acid or Brønsted acid) is included in the catalyst, lower operational temperatures may be used, favoring the isomerization over the less desired cracking reactions.

The noble metal component of the present catalyst provides a hydrogenation-dehydrogenation component to the catalyst. Metals having a strong hydrogenation function are preferred, especially platinum and the other noble metals such as palladium, rhodium, iridium, rhenium, although other metals capable of acting as a hydrogenation component may also be used, for example, nickel, tungsten or other metals of Group VIIIA of the Periodic Table (IUPAC Table), either singly, in mixtures or in combination with other metals. The amount of the noble metal component may be in the range 0.001 to 5 wt. % of the total catalyst, e.g., from 0.1 to 2 wt. %. Base metal hydrogenation components may be added in somewhat greater amounts. The hydrogenation component can be exchanged onto the support material, impregnated into it or physically admixed with it. If the metal is to be impregnated into or exchanged onto the support, it may be done, for example, by treating the support with a platinum metal-containing ion. Suitable platinum compounds include chloroplatinic acid, platinous chloride and various compounds containing the platinum ammine complex. The metal compounds may be either compounds in which the metal is present in the cation or anion of the compound; both types of compounds can be used. Platinum compounds in which the metal is in the form of a cation of cationic complex, e.g., $Pt(NH_3)_4Cl_2$ are particularly useful, as are anionic complexes such as the vanadate and metatungstate ions. Cationic forms of other metals are also useful since they may be exchanged onto the support or impregnated into it.

The catalyst may be subjected to a final calcination under conventional conditions in order to dehydrate the catalyst and to confer the required mechanical strength on the catalyst. Prior to use the catalyst may be subjected to presulfiding.

When a source of hydrogenation metal, such as $H_2PtCl_6$, is used as a source of a hydrogenation/dehydrogenation component in the present catalyst, it may be desirable to subject the present catalyst to extended reducing conditions, e.g., lasting more than 4 hours. Benefits of such extended reducing conditions are demonstrated in Examples which follow, especially in Examples 26–38.

Higher isomerization activity may be provided by the inclusion of an additional material having Lewis or Brønsted acid activity in the catalyst, especially when the catalyst comprises a porous binder material. For this purpose, both liquid and solid acid materials may be used. Examples of suitable additional acidic materials include aluminum trichloride, boron trifluoride and complexes of boron trifluoride, for example, with water, lower alcohols or esters. The maximum amount which may be added is set by the ability of the support material, especially the binder material, to sorb the added component and is readily determined by experiment.

The present catalyst may be used as the exclusive isomerization catalyst in single or multiple catalyst beds or it may be used in combination with other isomerization catalysts. For example, a feed may be first contacted with a catalyst bed comprising the present catalyst followed by contact with a second catalyst bed comprising a different catalyst, such as Pt on mordenite, Pt on zeolite beta or a chlorided platinum-alumina catalyst, as described in U.S. Pat. Nos. 4,783,575 and 4,834,866. The temperature of the first catalyst bed may be higher than the temperature of the second catalyst bed. When the present catalyst is called upon to cause extensive ring opening, especially in an initial catalyst bed, relatively high temperatures, e.g., as high as 500° C., and/or relatively high pressures, e.g., as high as 200 atmospheres, may be employed.

The present catalyst can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the catalyst can be extruded before drying or partially dried and then extruded. The present catalyst may be composited with a matrix material to form the finished form of the catalyst and for this purpose conventional matrix materials such as alumina, silica-alumina and silica are suitable with preference given to silica as a non-acidic binder. Other binder materials may be used, for example, titania, zirconia and other metal oxides or clays. The active catalyst may be composited with the matrix in amounts from 80:20 to 20:80 by weight, e.g., from 80:20 to 50:50 active catalyst:matrix. Compositing may be done by conventional means including mulling the materials together followed by extrusion of pelletizing into the desired finished catalyst particles.

The catalyst may be treated by conventional pre-sulfiding treatments, e.g., by heating in the presence of hydrogen sulfide, to convert oxide forms of the metal components to their corresponding sulfides.

Although the use of the present catalyst in isomerization reactions has been emphasized hereinabove, it will be appreciated that this catalyst is useful for a variety of organic, e.g., hydrocarbon, compound conversion processes, especially those requiring the use of a dual-functional (1) acidic and (2) hydrogenation/dehydrogenation catalyst. Such conversion processes include, as non-limiting examples, hydrocracking hydrocarbons with reaction conditions including a temperature of from about 100° C. to about 700° C., a pressure of from about 0.1 atmosphere (bar) to about 30 atmospheres, a weight hourly space velocity of from about 0.1 to about 20, and a hydrogen/hydrocarbon mole ratio of from about 0 to about 20; dehydrogenating hydrocarbon compounds with reaction conditions including a temperature of from about 300° C. to about 700° C., a pressure of from about 0.1 atmosphere to about 10 atmospheres and a weight hourly space velocity of from about 0.1 to about 20; converting paraffins to aromatics with reaction conditions including a temperature of from about 100° C. to about 700° C., a pressure of from about 0.1 atmosphere to about 60 atmospheres, a weight hourly space velocity of from about 0.5 to about 400 and a hydrogen/hydrocarbon mole ratio of from about 0 to about 20; converting olefins to aromatics, e.g., benzene, toluene and xylenes, with reaction conditions including a temperature of from about 100° C. to about 700°

C., a pressure of from about 0.1 atmosphere to about 60 atmospheres, a weight hourly space velocity of from about 0.5 to about 400 and a hydrogen/hydrocarbon mole ratio of from about 0 to about 20; transalkylating aromatic hydrocarbons in the presence of polyalkylaromatic hydrocarbons with reaction conditions including a temperature of from about 200° C. to about 500° C., a pressure of from about atmospheric to about 200 atmospheres, a weight hourly space velocity of from about 10 to about 1000 and an aromatic hydrocarbon/polyalkylaromatic hydrocarbon mole ratio of from about 0.3/1 to about 20/1, and a hydrogen/hydrocarbon mole ratio of from about 0 to about 20; and transferring hydrogen from paraffins to olefins with reaction conditions including a temperature from about −25° C. to about 400° C., e.g., from about 75° C. to about 200° C., a pressure from below atmospheric to about 5000 psig, e.g., from about atmospheric to about 1000 psig, a mole ratio of total paraffin to total olefin of from about 1:2 to about 500:1, e.g., from about 5:1 to about 100:1; and a weight hourly space velocity based on olefin of from about 0.01 to about 100, e.g., from about 0.05 to about 5.

The present catalyst may also be used in various hydroprocessing reactions, such as the removal of metals, nitrogen and/or sulfur from feedstocks, such as resids, including such elements, particularly in the form of heteroatoms. These hydroprocessing reactions comprise contacting the feedstock along with a sufficient amount of hydrogen with the present catalyst under conditions sufficient to remove metals, nitrogen, and/or sulfur.

EXAMPLE 1

This Example describes the preparation of a tungstate modified zirconia catalyst. One part by weight of zirconyl chloride, $ZrOCl_2 \cdot 8H_2O$, was added to 3 parts by weight of a 10M $NH_4OH$ solution. The resulting slurry, $Zr(OH)_4$, was filtered and washed with 5 parts of distilled deionized water, then air dried at 140° C. for 8 hours. Approximately 7.5 parts by weight of the resulting $Zr(OH)_4$ were impregnated via incipient wetness with 2.2 parts of an aqueous solution containing 1 part of ammonium metatungstate, $(NH_4)_6H_6W_{12}O_{40}$. The resulting material was dried for 2 hours at 120° C. and then calcined at 800° C. in flowing air for 2 hours. The sample was calcined at 500° C. for 1 hour under flowing nitrogen prior to catalytic testing. This sample had a calculated mole ratio of $ZrO_2/WO_3$ of 11.6.

EXAMPLE 2

A platinum and tungstate modified zirconia catalyst was prepared by incipient wetness co-impregnation of $H_2PtCl_6$ and $(NH_4)_6H_6W_{12}O_{40}$ onto $Zr(OH)_4$. More particularly, to 181.8 parts by weight of $Zr(OH)_4$ were added, via incipient wetness impregnation, 54.5 parts of an aqueous solution containing 24.4 parts of $(NH_4)_6H_6W_{12}O_{40}$ and 1 part of $H_2PtCl_6$. The resulting material was then dried for 2 hours at 120° C., and then air calcined at 800° C. for 2 hours. This platinum-containing catalyst was calcined at 500° C. for 1 hour in flowing nitrogen and then reduced with flowing hydrogen at 300° C. for approximately 2 hours prior to catalytic testing. This catalyst had a calculated mole ratio of $ZrO_2/WO_3$ of 11.6 and contained 100 ppm of Pt based on the total weight of the catalyst.

EXAMPLE 3

A catalyst was prepared in the same manner as in Example 2 except that more $H_2PtCl_6$ was used in the co-impregnation step. This catalyst had a calculated mole ratio of $ZrO_2/WO_3$ of 11.6 and contained 0.2 wt. % of Pt based on the total weight of the catalyst.

EXAMPLE 4

A catalyst was prepared in the same manner as in Example 2 except that more $H_2PtCl_6$ was used in the co-impregnation step. This catalyst had a calculated mole ratio of $ZrO_2/WO_3$ of 11.6 and contained 2 wt. % of Pt based on the total weight of the catalyst.

EXAMPLES 5–8

The catalysts of Examples 1–4 were tested in the isomerization of n-hexane. The n-hexane isomerization reactions were carried out in a fixed-bed down-flow reactor. Liquid n-hexane was fed into the reactor using a high pressure pump. Hydrogen was charged through a mass flow controller. Products were analyzed by gas chromatography. The experiments were performed at 260° C., LHSV=1.8 cc n-$C_6$ per cc catalyst per hour, 450 psig, and a $H_2$/n-$C_6$ mol ratio of 1.4.

The experimental results shown in Table 1 indicate that the addition of small amounts of platinum to the catalyst greatly improves the n-hexane isomerization activity to yield the desirable high-octane dimethyl butanes.

In the Tables which follow, the following abbreviations will be understood: n-$C_6$ (n-hexane); 3-MP (3-methylpentane); 2-MP (2-methylpentane); 2,3-DMB (2,3-dimethylbutane); 2,2-DMB (2,2-dimethylbutane); i-$C_5$ (isopentane); n-$C_5$ (n-pentane); $C_4$-(hydrocarbons having 4 or less carbon atoms); $C_7$+ (hydrocarbons having 7 or more carbon atoms); CH (cyclohexane); MCP (methylcyclopentane); BZ (benzene); $C_3$- (hydrocarbons having 3 or less carbon atoms); i-$C_4$ (isobutane); n-$C_4$ (n-butane); and $C_5$+ (hydrocarbons having 5 or more carbon atoms).

TABLE 1

| Example | Catalyst | Conv. (wt. %) | n-$C_6$ | 3-MP | 2-MP | 2,3-DMB | 2,2-DMB | i-$C_5$ | n-$C_5$ | $C_4$— | Other* |
| --- | --- | --- | --- | --- | --- | --- | --- | --- | --- | --- | --- |
| 5 | Example 1 | 67.1 | 32.9 | 19.1 | 28.9 | 7.8 | 3.7 | 2.9 | 0.6 | 2.0 | 2.0 |
| 6 | Example 2 | 73.2 | 26.8 | 21.3 | 32.2 | 8.8 | 4.7 | 2.5 | 0.5 | 1.2 | 2.0 |
| 7 | Example 3 | 79.9 | 20.1 | 20.3 | 30.0 | 8.0 | 9.3 | 4.9 | 1.6 | 3.4 | 2.2 |
| 8 | Example 4 | 84.3 | 15.7 | 18.7 | 29.1 | 8.5 | 15.5 | 5.4 | 1.7 | 2.3 | 3.2 |

*Other is $C_7$+, cyclohexane (CH), and methylcyclopentane (MCP)

EXAMPLES 9 and 10

The catalyst of Example 3 (0.2 wt. % Pt and a calculated mole ratio of $ZrO_2/WO_3$ of 11.6) was tested at lower temperature, 220° C., and lower LHSV. The results are presented in Table 2 and indicate that high yields of isomerate are obtained.

n-hexane isomerization over the catalyst of Example 13. A synthetic feedstock having the composition given in Table 4

TABLE 2

| Example | LHSV (hr$^{-1}$) | Conv. (wt. %) | n-C$_6$ | 3-MP | 2-MP | 2,3-DMB | 2,2-DMB | i-C$_5$ | n-C$_5$ | C$_4$— | Other* |
|---|---|---|---|---|---|---|---|---|---|---|---|
| 9 | 0.4 | 86.4 | 13.6 | 16.8 | 26.5 | 7.8 | 16.7 | 8.0 | 2.8 | 4.8 | 2.9 |
| 10 | 0.6 | 83.1 | 16.9 | 20.1 | 31.8 | 9.3 | 11.7 | 3.7 | 0.7 | 2.5 | 3.2 |

*Other is C$_7$+, cyclohexane (CH), and methylcyclopentane (MCP)

EXAMPLE 11

In this Example platinum was added to the tungstate modified zirconia material after the 800° C. air calcination step. 72.5 parts by weight of Zr(OH)$_4$, preparation given in Example 1, were impregnated with 21.7 parts of an aqueous solution containing 12.2 parts of (NH$_4$)$_6$H$_6$W$_{12}$O$_{40}$. The resulting material was dried for 2 hours at 120° C. and then calcined in air at 800° C. for 2 hours. After cooling to room temperature, a second incipient wetness impregnation was performed; this time, 1 part of H$_2$PtCl$_6$ dissolved in 21.7 parts of distilled water were added. The catalyst was dried at 120° C. for 2 hours, calcined in flowing air at 350° C. for 3 hours, and then reduced with hydrogen at 300° C. for approximately 2 hours. This catalyst contained 0.5 wt. % of Pt based on the total weight of the catalyst.

EXAMPLE 12

The platinum and tungstate modified catalyst of Example 11 was tested for n-hexane isomerization at 260° C., 450 psig, LHSV=0.6 hr$^{-1}$, and a H$_2$/n-C$_6$ mole ratio of 1.4. Results are given in Table 3.

was used in these experiments. The product composition and operating conditions are presented in Table 5. Results indicate that the catalyst of this invention exhibits high activity for ring opening, while maintaining high C$_5$+ yield and high paraffin isomerization selectivity to more highly branched paraffins.

TABLE 4

FEED COMPOSITION

| Component | Wt. % |
|---|---|
| n-Hexane (n-C$_6$) | 50.0 |
| Methylcyclopentane (MCP) | 14.5 |
| Cyclohexane (CH) | 31.7 |
| Benzene (BZ) | 3.9 |

TABLE 3

| Example | Catalyst | Conv. (wt. %) | n-C$_6$ | 3-MP | 2-MP | 2,3-DMB | 2,2-DMB | i-C$_5$ | n-C$_5$ | C$_4$— | Other* |
|---|---|---|---|---|---|---|---|---|---|---|---|
| 12 | Example 11 | 83.4 | 16.6 | 19.6 | 29.9 | 8.3 | 17.5 | 3.4 | 1.5 | 2.9 | traces |

*Other is C$_7$+, cyclohexane (CH), and methylcyclopentane (MCP)

EXAMPLE 13

Zirconium hydroxide, Zr(OH)$_4$, was synthesized by rapidly hydrolyzing Zr(O)Cl$_2$ in a 10M NH$_4$OH solution. The slurry was then pulverized for 30 minutes, filtered, washed with DI water, vacuum dried for 4 hours, and dried at 140° C. for 8 hours.

Tungstate modified zirconia was prepared by impregnating Zr(OH)$_4$ with ammonium metatungstate, (NH$_4$)$_6$H$_6$W$_{12}$O$_{40}$. Drying of the resultant sample was performed for 2 hours at 120° C. and then calcined at 800° C. The material was cooled down to ambient temperature before Pt was added via incipient wetness using H$_2$PtCl$_6$. The platinum-containing catalyst was calcined at 400° C. for 2 hours in flowing air, and then reduced with flowing hydrogen at 300° C. for approximately 2 hours. The catalyst had a calculated mole ratio of ZrO$_2$/WO$_3$ of 11.6 and contained 0.5 wt. % Pt based on the total weight of the catalyst.

EXAMPLES 14 and 15

These Examples illustrate the results obtained on simultaneous ring opening of C$_6$ cyclic hydrocarbons and

TABLE 5

| Example | 2 | 3 |
|---|---|---|
| Reaction Conditions | | |
| Reactor temperature (°C.) | 260 | 288 |
| Reactor pressure (psig) | 450 | 450 |
| LHSV (hr$^{-1}$) | 0.54 | 0.54 |
| H$_2$/C$_6$-mixture (mol/mol) | 2 | 2 |
| Product Composition (wt. %) | | |
| C$_3$— | tr | 0.7 |
| i-C$_4$ | 1.3 | 5.3 |
| n-C$_4$ | 0.4 | 2.0 |
| i-C$_5$ | 2.4 | 7.5 |
| n-C$_5$ | 0.9 | 3.7 |
| 2,2-DMB | 9.3 | 11.4 |
| 2,3-DMB | 6.1 | 6.2 |
| 2-MP | 22.3 | 22.8 |
| 3-MP | 14.7 | 15.3 |
| n-C$_6$ | 12.6 | 13.5 |
| MCP | 20.4 | 8.4 |
| CH | 6.3 | 2.0 |

TABLE 5-continued

| Example | 2 | 3 |
|---|---|---|
| BZ | 0 | 0 |
| $C_7+$ | 3.3 | 1.1 |
| $C_5+$ Yield (wt. %) | 98.3 | 92.0 |
| Reactant Conversion (%) | | |
| Ring Opening | 46.6 | 79.2 |
| n-$C_6$ | 74.8 | 73.0 |

EXAMPLE 16

This Example describes the preparation of a hydrous $ZrO_2$ support. One part by weight of zirconyl chloride, $ZrOCl_2$, $8H_2O$, was dissolved in 10 parts $H_2O$ and concentrated $NH_4OH_{(aq)}$ added until the solution pH was ~9. The resulting slurry, $Zr(OH)_4$, was filtered and washed with 10 parts of distilled, deionized water. The solid was air dried at 130° C. for 16 hours.

EXAMPLE 17

This Example describes the preparation of a $WO_x/ZrO_2$ catalyst from the zirconia support described in Example 16. Approximately 5.6 parts by weight of the dried product from Example 16 was impregnated via incipient wetness with 4.2 parts of an aqueous solution containing 1 part of ammonium metatungstate, $(NH_4)_6H_6W_{12}O_{40}$. The resulting material was dried in air and then calcined at 825° C. in air for 3 hours.

EXAMPLE 18

This Example describes the preparation and use of a $Pt/WO_x/ZrO_2$ catalyst from the resultant product described in Example 17. To 1 part of an 8% $H_2PtCl_6$ solution was added 2.5 parts of $H_2O$. This mixture was then used to impregnate by incipient wetness 7 parts of the dried product (at 130° C.) from Example 17. The catalyst was then calcined at 300° C. in air for 2 hours. This catalyst was designated Catalyst A. In the catalytic experiments, Catalyst A was reduced with $H_2$ (100 cc/min) at 300° C. and atmospheric pressure for 4 hours. The unit was then brought to the desired conditions and hexane feed introduced. Catalytic data and results are given in Table 6.

EXAMPLE 19

This Example describes the preparation of another $WO_x/ZrO_2$ catalyst using the zirconia support described in Example 16. Approximately 2.4 parts by weight of the dried product from Example 16 was impregnated via incipient wetness with 2.6 parts of an aqueous solution containing 1 part of ammonium metatungstate. The resulting material was dried in air and then calcined at 825° C. in air for 3 hours.

EXAMPLE 20

This Example describes the preparation and use of a $Pt/WO_x/ZrO_2$ catalyst from the resultant product described in Example 19. To 1 part of an 8% $H_2PtCl_6$ solution was added 2.5 parts of $H_2O$. This mixture was then used to impregnate by incipient wetness 7 parts of the dried product (at 130° C.) from Example 19. The catalyst was then calcined at 300° C. in air for 2 hours. This catalyst was designated Catalyst B. In the catalytic experiments, Catalyst B was reduced with $H_2$ (100 cc/min) at 300° and atmospheric pressure for 18 hours. The unit was then brought to the desired conditions and hexane feed introduced. Catalytic data and results are given in Table 7.

EXAMPLE 21

This Example describes the preparation of the base-treated zirconia support. One part by weight of the filtered wet cake from Example 16 was mixed with 10 parts of distilled, deionized water and the pH of the mixture set to pH ~9 with concentrated $NH_4OH_{(aq)}$. This mixture was refluxed for 16 hours, cooled, filtered, and washed with 10 parts of water. The solid was air dried at 130° C. for 16 hours.

EXAMPLE 22

This Example describes the preparation of a $WO_x/ZrO_2$ catalyst from the zirconia support described in Example 21. Approximately 5.6 parts by weight of the dried product from Example 21 was impregnated via incipient wetness with 4.2 parts of an aqueous solution containing 1 part of ammonium metatungstate. The resulting material was dried in air and then calcined at 825° C. in air for 3 hours.

EXAMPLE 23

This Example describes the preparation and use of a $Pt/WO_x/ZrO_2$ catalyst from the resultant product in Example 22. To 1 part of an 8% $H_2PtCl_6$ solution was added 2.5 parts of $H_2O$. This mixture was then used to impregnate by incipient wetness 7 parts of the dried product (at 130° C.) from Example 22. The catalyst was then calcined at 300° C. in air for 2 hours. This catalyst was designated Catalyst C. In the catalytic experiments, Catalyst C was reduced with $H_2$ (100 cc/min) at 300° C. and atmospheric pressure for 4 hours. The unit was then brought to the desired conditions and hexane feed introduced. Catalytic data and results are given in Table 8.

EXAMPLE 24

This Example describes the preparation of another $WO_x/ZrO_2$ catalyst using the zirconia support described in Example 21. Approximately 3.4 parts by weight of the dried product from Example 21 was impregnated via incipient wetness with 2.6 parts of an aqueous solution containing 1 part of ammonium metatungstate. The resulting material was dried in air and then calcined at 825° C. in air for 3 hours.

EXAMPLE 25

This Example describes the preparation and use of a $Pt/WO_x/ZrO_2$ catalyst from the resultant product described in Example 24. To 1 part of an 8% $H_2PtCl_6$ solution was added 2.5 parts of $H_2O$. This mixture was then used to impregnate by incipient wetness 7 parts of the dried product (at 130° C.) from Example 24. The catalyst was then calcined at 300° C. in air for 2 hours. This catalyst was designated Catalyst D. In the catalytic experiments, Catalyst D was reduced with $H_2$ (100 cc/min) at 300° C. and atmospheric pressure for 18 hours. The unit was then brought to the desired conditions and hexane feed introduced. Catalytic data and results are given in Table 9.

At comparable $H_2$ reduction times, the catalysts which were treated by heating with base solution (Catalysts C and D) showed improved yields of the isomerized 2,2-dimethylbutane product over the untreated catalysts (Catalysts A and B) at varying temperatures.

TABLE 6

Catalytic Data for Hexane Isomerization with Catalyst A

| Temperature, °C. | 230 | 240 |
|---|---|---|
| Pressure, psig | 450 | 450 |
| LHSV | 0.6 | 0.6 |
| $H_2$/HC | 1.4/1 | 1.4/1 |
| Hexane conv., wt. % | 70.6 | 77.9 |
| Selectivity, wt. % | | |
| $C_1$–$C_5$ | 0.5 | 0.8 |
| 2,2-dimethylbutane | 7.9 | 11.6 |
| 2,3-dimethylbutane | 11.1 | 12.0 |
| 2-methylpentane | 49.3 | 46.1 |
| 3-methylpentane | 31.2 | 29.5 |
| Yield, wt. % | | |
| 2,2-dimethylbutane | 5.6 | 9.0 |

TABLE 7

Catalytic Data for Hexane Isomerization with Catalyst B

| Temperature, °C. | 200 | 210 | 220 | 230 |
|---|---|---|---|---|
| Pressure, psig | 450 | 450 | 450 | 450 |
| LHSV | 0.6 | 0.6 | 0.6 | 0.6 |
| $H_2$/HC | 1.4/1 | 1.4/1 | 1.4/1 | 1.4/1 |
| Hexane conv., wt. % | 80.5 | 82.0 | 82.9 | 84.0 |
| Selectivity, wt. % | | | | |
| $C_1$–$C_5$ | 0.4 | 1.2 | 2.0 | 2.8 |
| 2,2-dimethylbutane | 12.6 | 14.8 | 19.9 | 21.8 |
| 2,3-dimethylbutane | 13.0 | 12.6 | 11.8 | 11.6 |
| 2-methylpentane | 45.8 | 43.6 | 40.4 | 37.8 |
| 3-methylpentane | 28.2 | 27.8 | 25.9 | 23.9 |
| Yield, wt. % | | | | |
| 2,2-dimethylbutane | 10.1 | 12.1 | 16.5 | 18.4 |

TABLE 8

Catalytic Data for Hexane Isomerization with Catalyst C

| Temperature, °C. | 230 | 240 |
|---|---|---|
| Pressure, psig | 450 | 450 |
| LHSV | 0.6 | 0.6 |
| $H_2$/HC | 1.4/1 | 1.4/1 |
| Hexane conv., wt. % | 80.4 | 81.7 |
| Selectivity, wt. % | | |
| $C_1$–$C_5$ | 0.5 | 1.4 |
| 2,2-dimethylbutane | 14.7 | 19.0 |
| 2,3-dimethylbutane | 12.2 | 11.8 |
| 2-methylpentane | 44.1 | 40.9 |
| 3-methylpentane | 28.5 | 26.9 |
| Yield, wt. % | | |
| 2,2-dimethylbutane | 11.9 | 15.5 |

TABLE 9

Catalytic Data for Hexane Isomerization with Catalyst D

| Temperature, °C. | 200 | 210 | 220 | 230 |
|---|---|---|---|---|
| Pressure, psig | 450 | 450 | 450 | 450 |
| LHSV | 0.6 | 0.6 | 0.6 | 0.6 |
| $H_2$/HC | 1.4/1 | 1.4/1 | 1.4/1 | 1.4/1 |
| Hexane conv., wt. % | 81.9 | 82.1 | 83.4 | 84.3 |
| Selectivity, wt. % | | | | |
| $C_1$–$C_5$ | 0.9 | 1.1 | 2.5 | 6.5 |
| 2,2-dimethylbutane | 18.3 | 18.1 | 22.5 | 23.4 |
| 2,3-dimethylbutane | 12.3 | 12.3 | 11.4 | 10.6 |
| 2-methylpentane | 41.7 | 41.6 | 38.6 | 36.2 |
| 3-methylpentane | 26.7 | 26.9 | 25.0 | 23.3 |
| Yield, wt. % | | | | |
| 2,2-dimethylbutane | 15.0 | 14.8 | 18.8 | 19.7 |

EXAMPLE 26

This Example describes the preparation of a hydrous zirconia support. One part by weight of zirconyl chloride, $ZrOCl_2 \cdot 8H_2O$, was dissolved in 10 parts $H_2O$ and concentrated $NH_4OH_{(aq)}$ added until the solution pH was ~9. The resulting slurry, $Zr(OH)_4$, was filtered and washed with 10 parts of distilled, deionized water. The solid was mixed with 10 parts of distilled, deionized water, and the pH of the mixture set to pH ~9 with $NH_4OH_{(aq)}$. This mixture was refluxed for 16 hours, cooled, filtered, and washed with 10 parts of water. The solid was air dried at 130° C. for 16 hours.

EXAMPLE 27

This Example describes the preparation of a $WO_x/ZrO_2$ catalyst from the zirconia support described in Example 26. Approximately 3.3 parts by weight of the dried product from Example 26 was impregnated via incipient wetness with 2.6 parts of an aqueous solution containing 1 part of ammonium metatungstate. The resulting material was dried in air and then calcined at 825° C. in air for 3 hours. The resultant product was designated Catalyst E.

EXAMPLE 28

Catalyst F was prepared analogously to Catalyst E except 1.17 parts of ammonium metatungstate was used.

EXAMPLE 29

Catalyst G was prepared analogously to Catalyst E except 1.67 parts of ammonium metatungstate was used.

EXAMPLES 30–32

After calcining, Catalysts E, F, and G were then impregnated with Pt via incipient wetness using a solution of 2.5 parts $H_2O$ and 1 part 8% $H_2PtCl_6$. The catalysts were air dried and then calcined at 300° C. in air for 2 hours.

EXAMPLES 33 and 34

Catalyst E from Example 30 was tested for hexane isomerization. In two separate runs, prior to contacting with feed hexane, the fresh catalyst was treated with $H_2$ (100 cc/min) at 300° C. for 4 and 18 hours. Experimental conditions and catalyst results are given in Table 10.

EXAMPLES 35 and 36

Catalyst F from Example 31 was tested for hexane isomerization analogously to Examples 33 and 34. Experimental conditions and catalytic results are given in Table 11.

EXAMPLES 37 and 38

Catalyst G from Example 32 was tested for hexane isomerization. In two separate runs, prior to contacting with feed hexane, the fresh catalyst was treated with $H_2$ (100 cc/min) at 300° C. for 4 and 72 hours. Experimental conditions and catalytic results are given in Table 12.

For Catalysts E, F, and G, increased yields of isomerized product at constant temperature were observed with the same catalysts treated with hydrogen for 18 hours instead of 4 hours. For Catalyst G, an additional experiment involving $H_2$ pretreatement for 72 hours was performed. Although hexane isomerization activity was still present after the 72 hour pretreatment, the yield of 2,2-dimethylbutane was significantly lower at constant temperature than the yields obtained after 4 hours of $H_2$ pretreatment.

TABLE 10

Catalytic Data for Hexane Isomerization with Catalyst E

|  | 4 hours | | | 18 hours | | |
|---|---|---|---|---|---|---|
| Temperature, °C. | 200 | 220 | 200 | 210 | 220 | 230 |
| Pressure, psig | 450 | 450 | 450 | 450 | 450 | 450 |
| LHSV | 0.6 | 0.6 | 0.6 | 0.6 | 0.6 | 0.6 |
| $H_2$/HC | 1.4/1 | 1.4/1 | 1.4/1 | 1.4/1 | 1.4/1 | 1.4/1 |
| Hexane conv., wt. % | 75.3 | 82.0 | 80.5 | 82.0 | 82.9 | 84.0 |
| Selectivity, wt. % | | | | | | |
| $C_1$–$C_5$ | 0.2 | 1.6 | 0.4 | 1.2 | 1.8 | 4.8 |
| 2,2-dimethylbutane | 8.4 | 16.1 | 12.6 | 14.8 | 19.9 | 21.8 |
| 2,3-dimethylbutane | 13.1 | 12.3 | 13.0 | 12.6 | 11.8 | 11.6 |
| 2-methylpentane | 47.8 | 42.4 | 45.7 | 43.5 | 40.5 | 37.9 |
| 3-methylpentane | 30.5 | 27.6 | 28.1 | 27.7 | 26.0 | 23.9 |
| Yield, wt. % | | | | | | |
| 2,2-dimethylbutane | 6.3 | 13.2 | 10.1 | 12.1 | 16.5 | 18.4 |

TABLE 11

Catalytic Data for Hexane Isomerization with Catalyst F

|  | 4 hours | | | 18 hours | | |
|---|---|---|---|---|---|---|
| Temperature, °C. | 210 | 220 | 230 | 210 | 220 | 230 |
| Pressure, psig | 450 | 450 | 450 | 450 | 450 | 450 |
| LHSV | 0.6 | 0.6 | 0.6 | 0.6 | 0.6 | 0.6 |
| $H_2$/HC | 1.4/1 | 1.4/1 | 1.4/1 | 1.4/1 | 1.4/1 | 1.4/1 |
| Hexane conv., wt. % | 81.6 | 82.7 | 83.6 | 82.1 | 83.4 | 84.3 |
| Selectivity, wt. % | | | | | | |
| $C_1$–$C_5$ | 0.4 | 0.9 | 2.5 | 1.1 | 2.5 | 6.5 |
| 2,2-dimethylbutane | 9.5 | 17.4 | 21.6 | 18.1 | 22.5 | 23.4 |
| 2,3-dimethylbutane | 12.5 | 12.2 | 11.3 | 12.3 | 11.4 | 10.6 |
| 2-methylpentane | 47.4 | 42.2 | 39.3 | 41.6 | 38.6 | 36.2 |
| 3-methylpentane | 30.2 | 27.3 | 25.4 | 26.9 | 25.0 | 23.3 |
| Yield, wt. % | | | | | | |
| 2,2-dimethylbutane | 6.8 | 14.2 | 17.9 | 14.8 | 18.8 | 19.7 |

TABLE 12

Catalytic Data for Hexane Isomerization with Catalyst G

|  | 4 hours | | 72 hours | |
|---|---|---|---|---|
| Temperature, °C. | 200 | 220 | 200 | 220 |
| Pressure, psig | 450 | 450 | 450 | 450 |
| LHSV | 0.6 | 0.6 | 0.6 | 0.6 |
| $H_2$/HC | 1.4/1 | 1.4/1 | 1.4/1 | 1.4/1 |
| Hexane conv., wt. % | 79.8 | 84.5 | 48.9 | 76.7 |
| Selectivity, wt. % | | | | |
| $C_1$–$C_5$ | 0.5 | 3.1 | 0.0 | 0.4 |
| 2,2-dimethylbutane | 14.5 | 25.1 | 2.6 | 10.9 |
| 2,3-dimethylbutane | 21.0 | 11.3 | 11.1 | 12.7 |
| 2-methylpentane | 36.6 | 37.3 | 52.9 | 46.1 |
| 3-methylpentane | 27.4 | 23.3 | 33.4 | 29.9 |
| Yield, wt. % | | | | |
| 2,2-dimethylbutane | 11.6 | 21.3 | 1.3 | 8.44 |

What is claimed is:

1. A catalyst consisting essentially of (i) a hydrogenation/dehydrogenation component comprising a noble metal and (ii) an acidic solid component comprising zirconium oxide modified with an oxyanion of a Group VIB metal.

2. A catalyst according to claim 1, wherein said hydrogenation/dehydrogenation component, in addition to said noble metal, further comprises at least one non-noble metal in the form of at least one oxide, hydroxide or metal of at least one element selected from the group consisting of Group VIII metals, Group IVA metals, Group VB metals and Group VIIB metals.

3. A catalyst according to claim 1, wherein said hydrogenation/dehydrogenation component comprises platinum.

4. A catalyst according to claim 1, wherein said hydrogenation/dehydrogenation component further comprises tin.

5. A catalyst according to claim 1, wherein said Group VIB metal oxyanion is an oxyanion of molybdenum or tungsten.

6. A catalyst according to claim 1, wherein said hydrogenation/dehydrogenation component comprises platinum in the form of an oxide, hydroxide or free metal, and said Group VIB metal oxyanion is tungstate.

7. A catalyst according to claim 1 comprising a calculated mole ratio of $XO_2/YO_3$, where X is said zirconium and Y is said Group VIB metal, of up to 300 and from 0.001 wt % to about 5 wt % of said hydrogenation/dehydrogenation component, based upon the total weight of the catalyst.

8. A catalyst according to claim 6 comprising a calculated mole ratio of $XO_2/YO_3$, where X is said zirconium and Y is said Group VIB metal, of from 2 to 100 and from 0.001 wt % to about 5 wt % of said hydrogenation/dehydrogenation component, based upon the total weight of the catalyst.

9. A catalyst according to claim 6 comprising a calculated mole ratio of $XO_2/YO_3$, where X is said zirconium and Y is said Group VIB metal, of from 4 to 30 and from 0.1 wt % to about 2 wt % of platinum, based upon the total weight of the catalyst.

10. A method for preparing a catalyst consisting essentially of (i) a hydrogenation/dehydrogenation component comprising a noble metal and (ii) an acidic solid component comprising zirconium oxide modified with an oxyanion of a Group VIB metal, said method consisting essentially of the steps of:

(a) contacting a hydroxide or hydrated oxide of zirconium with an aqueous solution comprising an oxyanion of a Group VIB metal under conditions sufficient to form a solid material comprising oxygen, zirconium and Group VIB metal; and (b) combining said solid material of step (a) with a noble metal.

11. A method according to claim 10, wherein said aqueous solution of step (a) comprises a source of said oxyanion of a Group VIB metal which is $(NH_4)_2WO_2$ or $WCl_6$.

12. A method according to claim 10, wherein said aqueous solution of step (a) comprises a source of said oxyanion of a Group VIB metal which is selected from the group consisting of ammonium metatungstate, ammonium metamolybdate, tungsten chloride, molybdenum chloride, tungsten carbonyl, molybdenum carbonyl, tungstic acid, sodium tungstate and sodium molybdate.

13. A method according to claim 10, wherein the hydroxide of said zirconium is contacted with said aqueous solution according to step (a).

14. A method according to claim 13, wherein, prior to step (b), said solid material of step (a) is calcined under conditions sufficient to convert said hydroxide of said zirconium to an oxide of said zirconium.

15. A method according to claim 14, wherein step (b) comprises impregnating the calcined solid material of step (a) with $H_2PtCl_6$.

16. A method according to claim 13, wherein step (b) comprises impregnating the uncalcined solid material of step (a) with $H_2PtCl_6$.

17. A method according to claim 16, wherein the $H_2PtCl_6$ impregnated material of step (b) is calcined under conditions sufficient to convert said hydroxide of said zirconium to an oxide of said zirconium and to convert $H_2PtCl_6$ to platinum oxide, followed by subjecting the catalyst to reducing conditions sufficient to convert platinum to the metallic state.

* * * * *